United States Patent [19]

Nelson

[11] Patent Number: 4,497,827

[45] Date of Patent: Feb. 5, 1985

[54] ARACHIDONIC ACID ANALOGUES AS ANTI-INFLAMMATORY AND ANTI-ALLERGIC AGENTS

[75] Inventor: Peter H. Nelson, Los Altos, Calif.

[73] Assignee: Syntex (U.S.A.) Inc., Palo Alto, Calif.

[21] Appl. No.: 412,477

[22] Filed: Aug. 30, 1982

[51] Int. Cl.$^3$ .................. C07C 103/133; A61K 31/16
[52] U.S. Cl. .................................... 514/381; 260/404; 548/250; 568/312; 514/575; 514/627; 514/675
[58] Field of Search ................ 260/404; 424/320, 327

[56] References Cited

U.S. PATENT DOCUMENTS 3,427,316 2/1969 Wakeman et al. .................. 260/286
3,995,059 11/1976 Fukumaru et al. ............. 424/320 X
4,116,955 9/1978 Ichikawa et al. ............... 560/248 X

FOREIGN PATENT DOCUMENTS 785292 6/1972 Belgium .
2140369 1/1973 France .
2264522 10/1975 France .
6604058 9/1966 Netherlands .
711448 8/1968 Netherlands .
1074693 7/1967 United Kingdom .
1373463 11/1974 United Kingdom .

OTHER PUBLICATIONS

Inoue et al., CA 35:731' (1941).
Yamatsu et al., CA 96:6909g (1982).
Kraus et al., *C. R. Acad. Sc. Paris,* t. 295 Series II, pp. 761–763. (11/08/82).
Turcotte et al., *J. Med. Chem.,* 1975, vol. 18, No. 12, pp. 1184–1190 (1975).

*Primary Examiner*—Thomas A. Waltz
*Attorney, Agent, or Firm*—Alan M. Krubiner; Tom M. Moran; Charles L. Hartman

[57] ABSTRACT

Novel compounds of this invention are tetrazole, acylhydroxylamine, hydroxymethylketone and amide derivatives of unsaturated fatty acids which are selective inhibitors of the enzymes lipoxygenase and cyclooxygenase involved in the production of pain, inflammation, bronchoconstriction and allergic reactions. These compounds are beneficial in the treatment of a number of inflammatory and/or painful conditions and allergic reactions.

60 Claims, No Drawings

ARACHIDONIC ACID ANALOGUES AS ANTI-INFLAMMATORY AND ANTI-ALLERGIC AGENTS

BACKGROUND OF THE INVENTION

1. Field of the Invention

This invention concerns novel tetrazole, acylhydroxylamine, hydroxymethylketone and amide derivatives of unsaturated fatty acids and, where applicable, their pharmaceutically acceptable salts, their use in the prevention and treatment of inflammatory processes, pain and allergic reactions, and pharmaceutical compositions containing these compounds and methods of their preparation.

Arachidonic acid is the biological precursor of such pro-inflammatory agents as prostaglandins and leucotrienes, or the platelet aggregation inducers thromboxanes. Compounds of this invention show selective inhibitory activity on the enzymes involved in the metabolic synthetic pathways of prostaglandins, leucotrienes or thromboxanes. These compounds will be beneficial in the prevention or treatment of inflammatory and painful disorders, such as rheumatoid arthritis, or in the prevention or treatment of disorders of allergic origin, such as bronchospasm in asthma.

2. Related Disclosures

Those compounds closest in structure to those of the present invention are 2-descarboxy-2-(tetrazol-5-yl) prostaglandins disclosed in Dutch Pat. No. NL-7,211,860Q; N-(hydroxyalkyl) aliphatic amides disclosed in Belgium Pat. BE No. 785,292Q; Vitamin F compounds disclosed in French Pat. No. 2,264,522; long-chain fatty acid amides disclosed in French Pat. No. 2,140,369Q; unsaturated fatty acid amides disclosed in British Pat. No. 1,074,693 and 16-24 carbon unsaturated fatty acid amides disclosed in Dutch Pat. Neth. No. 6,604,058; quarternary ammonium hydroxamates are described in U.S. Pat. No. 3,427,316, and N-substituted fatty acid amides as cholesterol lowering agents are described in U.S. Pat. No. 3,995,059.

*J.Med.Chem.*, 12:1184(1975) describes analogs of lysophosphatidylethanolamine which inhibit renin activity. Eicosatetrayn-5,8,11,14-oic acid and its salts and esters are described in Belgium Pat. No. 711,448.

SUMMARY OF THE INVENTION

One aspect of this invention relates to compounds represented by the formulas (1), (2) and (3).

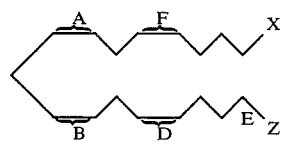

(1)

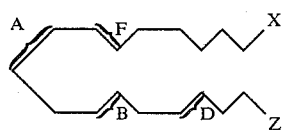

(2)

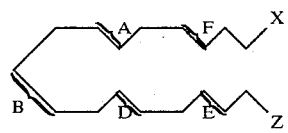

(3)

and their pharmaceutically acceptable salts wherein

A is C=C or C≡C;
B is C=C or C≡C;
D is C—C, C=C, or C≡C;
E is C—C, C=C, or C≡C;
F is C—C, C=C, or C≡C;
Z is —CH$_3$, —CH$_2$CH$_3$, —CH$_2$CH$_2$CH$_3$, —CH$_2$CH$_2$CH$_2$CH$_3$; and
X is 1-H-tetrazol-5-yl, C(O)NHOH, CONH$_2$ or C(O)CH$_2$OH.

Another aspect of this invention is a method of treating inflammation and allergic reactions in mammals by administering a therapeutically effective amount of a compound of formula (1), (2) or (3), or their pharmaceutically acceptable, non-toxic salts.

Still another aspect of this invention is a pharmaceutical composition containing a suitable pharmaceutical excipient and a compound of formula (1), (2) or (3), or its pharmaceutically acceptable, non-toxic salts.

Lastly, another aspect of this invention is a process for preparing compounds of formulas (1), (2) and (3), and their corresponding pharmaceutically acceptable, non-toxic salts, as discussed below.

DETAILED DESCRIPTION OF THE INVENTION

Definitions

As used herein "1-H-tetrazol-5-yl" means the compound N$_4$CH— wherein the H atom is attached to the tetrazole ring at position number 1 and the 1H-tetrazole ring is attached to the unsaturated aliphatic chain at the 5-position. The numbering of the heterocyclic ring follows the IUPAC numbering system.

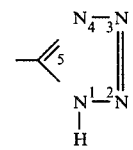

As used herein "acylhydroxylamine" represents the radical —C(O)NHOH. Acylhydroxylamines are also referred to as hydroxamic acids.

As used herein "hydroxymethylketone" represents the radical —C(O)CH$_2$OH.

As used hereinafter "unsaturated fatty acids" are fatty acids with 3 to 5 double or triple bonds in their carbon chain such as for example arachidonic acid, linolenic acid, eicosatrienoic acid, eicosatriynoic acid and such.

Carbons in fatty acids are numbered according to the IUPAC numbering system as illustrated below.

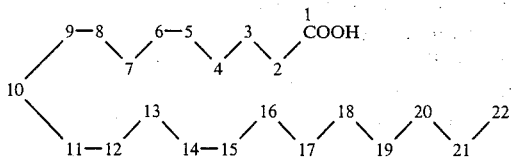

(Z) is used in its conventional fashion to denote the cis stereochemistry of double bonds and follows the number of the carbon atom from which the double bond emanates.

Classical nomenclature is used to name a compound having a triple bond as -ynyl and double bond as -enyl.

"Pharmaceutically acceptable, non-toxic salts" refers to salts derived from pharmaceutically acceptable, non-toxic inorganic and organic bases.

Exemplary names are given in the "Preferred Embodiment" section of this application.

PREFERRED EMBODIMENTS OF THE INVENTION

One group of preferred compounds of this invention is the compounds of formula (1):

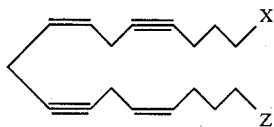

wherein X is 1-H-tetrazol-5-yl, C(O)NHOH, C(O)C-H$_2$OH or CONH$_2$, and Z is CH$_2$CH$_2$CH$_3$ or CH$_2$CH$_2$CH$_2$CH$_3$. Representative compounds of this group are 5-(eicosa-7(Z),13(Z)-diene-4,10-diynyl)-1-H-tetrazole; heneicosa-8(Z),14(Z)-diene-5,11-diynoylhydroxylamine; 1-hydroxydocosa-9(Z),15(Z)-diene-6,12-diyn-2-one; heneicosa-8(Z),14(Z)-diene-5,11-diynamide; docosa-8(Z),14(Z)-diene-5,11-diynamide; 5-(heneicosa-7(Z),13(Z)-diene-4,10-diynyl)-1-H-tetrazole; docosa-8(Z),14(Z)-diene-5,11-diynoylhydroxylamine; 1-hydroxytricosa-9(Z),15(Z)-diene-6,12-diyn-2-one.

Another group of preferred compounds of this invention are compounds of formula (1):

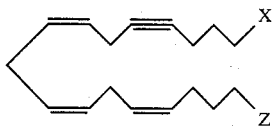

wherein X is 1-H-tetrazol-5-yl, C(O)NHOH, C(O)C-H$_2$OH or CONH$_2$ and Z is CH$_2$CH$_2$CH$_3$ or CH$_2$CH$_2$CH$_2$CH$_3$. Representative compounds of this group are 5-(eicosa-7(Z),10(Z),13(Z)-trien-4-ynyl)-1-H-tetrazole; heneicosa-8(Z),11(Z),14(Z)-trien-5-ynoylhydroxylamine; 1-hydroxydocosa-9(Z),12(Z),15(Z)-trien-6-yn-2-one; 5-(heneicosa-7(Z),10(Z),13(Z)-trien-4-ynyl)-1-H-tetrazole; docosa-8(Z),11(Z),14(Z)-trien-5-ynoylhydroxylamine; heneicosa-8(Z),11(Z),14(Z)-trien-5-ynamide; docosa-8(Z),11(Z),14(Z)-trien-5-ynamide; and 1-hydroxytricosa-9(Z),12(Z),15(Z)-trien-6-yn-2-one.

Other preferred compounds are those represented by formula (1)

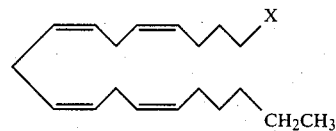

wherein X is 1-H-tetrazol-5-yl, C(O)NHOH, C(O)C-H$_2$OH or CONH$_2$. Compounds representative of this group are 5-(nonadeca-4(Z),7(Z),10(Z),13(Z)-tetraenyl)-1-H-tetrazole; eicosa-5(Z),8(Z),11(Z),14(Z)-tetraenoylhydroxylamine; 1-hydroxyheneicosa-6(Z),9(Z),12(Z),15(Z)-tetraen-2-one and eicosa-5(Z),8(Z),11(Z),14(Z)-tetraenamide.

More preferred compounds of this invention are the compounds of formula (1)

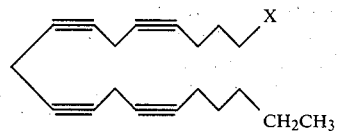

wherein X is 1-H-tetrazol-5-yl, C(O)NHOH, C(O)C-H$_2$OH or CONH$_2$. Representative compounds of this group are 5-(nonadeca-4,7,10,13-tetraynyl)-1-H-tetrazole; eicosa-5,8,11,14-tetraynoyl hydroxylamine; 1-hydroxyheneicosa-6,9,12,15-tetrayn-2-one; and eicosa-5,8,11,14-tetraynamide.

Most preferred compounds of this invention are compounds of formula (1)

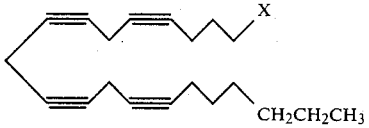

wherein X is 1-H-tetrazol-5-yl, C(O)NHOH, C(O)C-H$_2$OH or CONH$_2$. Compounds representative of this group are 5-(eicosa-4,7,10,13-tetraynyl)-1-H-tetrazole; heneicosa-5,8,11,14-tetraynoylhydroxylamine; 1-hydroxydocosa-6,9,12,15-tetrayn-2-one; and heneicosa-5,8,11,14-tetraynamide.

PREPARATION PROCEDURES

Preparation of fatty acid precursors with various combinations of double and triple bonds is known.

Isolation of twenty carbon eicosa-5(Z),8(Z),11(Z),14(Z)-tetraenoic acid (arachidonic acid) from organic materials is described in *J. Biol. Chem.*, 80, 455, (1928) and is hereby incorporated by reference.

Syntheses of nineteen carbon nonadeca-5(Z),8(Z),11(Z)14(Z)-tetraenoic acid and twenty-one carbon heneicosa-5(Z),8(Z),11(Z),14(Z)-tetraenoic acid are described in *Recueil*, 87, 461, (1968) and the references herein and are hereby incorporated by reference.

Preparations of octadeca-8(Z),11(Z),14(Z)-trienoic acid, nonadeca-8(Z),11(Z),14(Z)-trienoic acid, heneicosa-8(Z),11(Z),14(Z)-trienoic acid, and docosa-8(Z),11(Z),14(Z)-trienoic acid are described in *Recueil*, 87, 461, (1968) and the references therein and are hereby incorporated by reference.

Synthesis of octadeca-9,12,15-trienoic acid (linolenic acid) is described in *J. Chem. Soc.*, 4049 (1956) and the references therein and is hereby incorporated by reference.

Eicosa-5,8,11,14-tetraynoic acid preparation is described in *J. Chem. Soc.*, 2771 (1969) and is hereby incorporated by reference.

14,15-Dehydroarachidonic acid (eicosa-5(Z),8(Z),11(Z)-trien-14-ynoic acid) in which the 14,15 double bond is replaced by a triple bond, and its preparation is described in *J. Am. Chem. Soc.*, 104, 1750 (1982) and the references therein, and is hereby incorporated by reference.

5,6-,8,9-,11,12-Dehydroarachidonic acids and their syntheses are described in *J. Am. Chem. Soc.*, 104, 1952 (1982) and in *Tetrahedron Letters*, 23, 1651, (1982) and the references therein and is hereby incorporated by reference.

Eicosa-4(Z),8(Z),11(Z),14(Z)-tetraenoic acid; eicosa 5(Z),8(Z),11(Z),14(Z)-tetraenoic acid; eicosa-8(Z),11(Z),14(Z),18(Z)-tetraenoic acid; octadeca-5(Z),8(Z),11(Z),14(Z)-tetraenoic acid; docosa-5(Z),8(Z),11(Z),14(Z)-tetraenoic acid; nonadeca-4(Z),7(Z),10(Z),13(Z)-tetraenoic acid; eicosa-4,8,11,14-tetraynoic acid; octadeca-5,8,11,14-tetraynoic acid and their preparations are described in *Recueil*, 90, 943 (1971) and the references therein, and are hereby incorporated by reference.

Eicosa-8(Z),11(Z),14(Z)-trienoic acid, octadeca-6(Z),9(Z),12(Z)trienoic acid, nonadeca-8(Z),11(Z),14(Z)-trien-5-ynoic acid and their preparations are described in *Recueil* 94, 262 (1975) and the references therein and are hereby incorporated by reference.

Nonadecatrienoic acid, octadecatrienoic acid, and other substituted trienoic acids are described in *Recueil*, 94, 269 (1975) and *Recueil*, 87, 461 (1968) and the references therein, and are hereby incorporated by reference.

Synthesis of arachidonic acid and related higher unsaturated compounds are described in *Recueil*, 82, 1015 (1963) and the references therein and is hereby incorporated by reference.

The syntheses of naturally-occuring polyunsaturated fatty acids are described in *Progress in the Chemistry of Fats and Other Lipids*, 9(2), 119–157 (1966) Pergamon Press, Oxford, Publ., and in the references therein and are hereby incorporated by reference.

The syntheses of unsaturated fatty acids which are not specifically described in the references above may be accomplished by using the above described procedures but starting with appropriate different precursors of fatty acids.

Compounds of formula (1), (2) and (3) wherein B and F are C≡C; A and D are C═C, E is C—C, and X is COOH, which are intermediates in the synthesis of compounds of formula (1), (2), and (3), wherein B and F are C≡C, A and D are C═C, E is C—C, and X is 1-H-tetrazol-5-yl, C(O)NHOH; C(O)CH$_2$OH, and CONH$_2$ are made by reacting together a bis(halomagnesium) salt, preferably the bis(bromomagnesium) salt, of hex-5-ynoic acid, hept-6-ynoic acid, or pent-4-ynoic acid, with a 1-halo, preferably a 1-bromoalka-2,8-dien-5-yne. The reaction is conducted in an ethereal solvent, preferably tetrahydrofuran, at a temperature of from 0° C. to 65° C., preferably at 65° C., for from 1 to 72 hours, preferably about 24 hours. From 1 to 3, preferably 2 moles, of the acetylenic acid are used for each mole of the 1-haloalka-2,8-dien-5-yne. The reaction is conducted in the presence of a catalytic amount of a cuprous halide or cyanide, preferably cuprous chloride. The 1-haloalka-2,8-dien-5-ynes which are employed in the reaction are made from the corresponding 1-hydroxyalka-2,8-dien-5-ynes, by reaction with halogenating reagents such as triphenylphosphine/carbon tetrahalide, phosphorus trihalides, or triphenylphosphine/cyanogen bromide, preferably the latter. The reaction is conducted at from 0° C. to 50° C., preferably about 25° C., for from 1 to 24 hours, preferably about 4 hours, in an inert organic solvent, preferably methylene chloride. The halogenating reagent and the alcohol are present in equimolar amounts. The 1-hydroxyalka-2,8-dien-5-ynes are prepared from the corresponding 1-(tetrahydropyranyloxy)-alka-2,8-dien-5-ynes by treatment with an acid such as acetic acid, sulphuric acid, or p-toluenesulphonic acid, preferably the latter, in a water-miscible organic solvent, such as tetrahydrofuran, ethanol or methanol, preferably the latter, optionally in the presence of from 1% to 40%, preferably 5%, by volume, of water. The reaction is conducted at from 0° C. to 50° C., preferably about 25° C., for from ½ to 12 hours, preferably 2 hours. The 1-(tetrahydropyranyloxy)alka-2,8-dien-5-ynes are prepared by the Wittig reaction between the ylid generated from 1-(triphenylphosphonio)-alk-6-en-3-yne halides, for example 1-(triphenylphosphonio)-dodec-6-en-3-yne bromide, the preparation of which is described in *J. Am. Chem. Soc.*, 104, 1752 (1982), and 2-(tetrahydropyranyloxy)acetaldehyde, the preparation of which is described in *Chem. Pharm. Bull.*, 11, 188 (1963). The ylid is generated by reaction between the phosphonium halide and an equimolar amount of a strong base, for example, sodium hydride, phenyllithium or butyllithium, preferably butyllithium, in a solvent such as dimethylsulphoxide or tetrahydrofuran, preferably the latter, containing from 0% to 25%, preferably 10% by volume, of hexamethylphosphoric triamide at a temperature of from −100° C. to 25° C., preferably −78° C., for from half to 6 hours, preferably 1 hour. The 2-(tetrahydropyranyloxy)acetaldehyde and the phosphonium salt are used in equimolar amounts.

The 1-(tetrahydrofuranyloxy)-alka-2,8-dien-5-ynes are also prepared by the coupling reaction between a 1-haloalk-2-ene, for example, 1-bromooct-2-ene, the preparation of which is described in *J. Chem. Soc.*, 3868 (1957) and 1-(tetrahydropyranyloxy)hex-2-en-5-yne. The coupling reaction is conducted in an aqueous or aqueous alcoholic solution, at a temperature of from 0° C. to about 100° C., optionally in the presence of a cuprous salt, for example, cuprous chloride, for from 1 to 24 hours. 1-(Tetrahydropyranyloxy)hex-2-en-5-yne is obtained by the acid-catalyzed reaction between dihydropyran and hex-2-en-5-yn-1-ol, the preparation of which is described in *Bull. Soc. Chem. France*, 2105 (1963). The reaction is conducted either without solvent or in the presence of an organic solvent such as ether or methylene chloride, in the presence of an acid catalyst such as sulphuric acid, hydrochloric acid or phosphorus oxychloride.

Compounds wherein X is 1-H-tetrazol-5-yl and CONH$_2$ are prepared according to the Reaction Scheme 1.

REACTION SCHEME 1

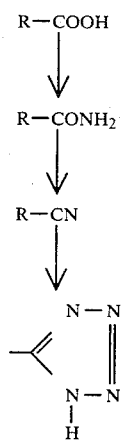

R-COOH is an unsaturated fatty acid of the formula (1), (2) or (3) wherein
A is C=C or C≡C;
B is C=C or C≡C;
D is C—C, C=C, or C≡C;
E is C—C, C=C, or C≡C;
F is C—C, C=C, or C≡C; and
X is COOH.

In the following description the Roman numerals in parentheses show the steps in the Reaction Scheme.

Preparation of tetrazole derivatives of various unsaturated fatty acids of 18–22 carbon chain begins with the reaction of an appropriate unsaturated fatty acid of formula (1), (2) or (3), X is COOH, for example arachidonic acid, with carbonyldiimidazole in the molar ratio of 1:1 in an aprotic organic solvent, preferably dichloromethane, for a period of 1–7 hours, preferably 4 hours. Then the product of the reaction is reacted with a large excess of ammonium hydroxide for 24–64 hours, preferably for 48 hours. Eicosa-5(Z),8(Z),11(Z),14(Z)-tetraenamide (II) or any other unsaturated fatty acid amide (depending on the initially used unsaturated fatty acid) is obtained using separation procedures known in the art.

To a solution of compound (II) in a basic organic solvent, preferably pyridine, is added an organic sulphonyl halide, preferably p-toluenesulphonyl chloride in a molar ratio 1:1. The mixture is reacted for 12–48 hours, preferably 24 hours, and the solution is poured into water. Eicosa 5(Z),8(Z),11(Z),14(Z) tetraenenitrile (III) or any other fatty acid nitrile, is extracted from the aqueous phase with an organic solvent, preferably ethyl ether, and the extract is purified by procedures known in the art.

Compound (III) is then reacted with an excess, preferably 3 moles, of an alkali metal azide, preferably sodium azide, and an excess, preferably 3 moles, of an ammonium halide, preferably ammonium chloride, in an aprotic polar solvent, preferably dimethylformamide, at a temperature of 80° C. to 120° C., preferably 100° C., for 16 to 48 hours, preferably 24 hours optionally in the presence of a Lewis acid such as, for example, boron trifluoride.

The product, 5-(nonadeca-4(Z),7(Z),10(Z),13(Z) tetraenyl)-1-H-tetrazole (IV) is then isolated by procedures known in the art.

Tetrazole derivatives of other unsaturated fatty acids are obtained by the same procedure wherein one of those unsaturated fatty acids described in formulas (1), (2), and (3), wherein X is COOH is used as the starting material.

Preparation of amide derivatives of unsaturated fatty acids can be alternately effected by first converting the acid into an activated derivative such as, for example, an acyl halide, an anhydride, a mixed anhydride, an alkyl ester, a substituted or unsubstituted phenyl ester, a thioalkyl ester, a thiophenyl ester, an acyl imidazole, and the like. The activated derivative is then reacted with ammonia or aqueous ammonia with or without a suitable water-miscible or immiscible organic solvent, for example, methanol, ethanol, dichloromethane, and the like, so as to produce the amide. The reaction is conducted at from −30° C. to the boiling point of the solvent or solvent mixture used, for from 1 to 96 hours. Alternatively, the amide can be made by heating together the unsaturated fatty acid and ammonia, or by heating the ammonium salt of the unsaturated fatty acid. The reaction is conducted either in the absence of a solvent, or in the presence of a solvent such as, for example, toluene, at a temperature of from 100° C. to 300° C., for from 1 to 12 hours. Alternatively, the amide can be obtained by hydrolysis of the nitrile of an unsaturated fatty acid, using either inorganic or organic acids or bases, such as, for example, hydrochloric acid, sulphuric acid, p-toluenesulphonic acid, sodium hydroxide, potassium carbonate, or tetrabutylammonium hydroxide and the like. The reaction is conducted in water optionally containing from 1% to 95% of a cosolvent such as, for example, methanol, acetic acid or diglyme, at a temperature of from 0° C. to the boiling point of the solvent used, for from 1 to 96 hours. Such procedures are well known to those skilled in the art and are described, for example, in *Synthetic Organic Chemistry*, John Wiley and Sons, Publ., New York, 565–590 (1953) and *Compendium of Organic Synthetic Methods*, Vol. 1, Wiley-Interscience, New York, 203–230 (1971).

Tetrazole derivatives of unsaturated fatty acids can alternately be prepared by the reaction between an iminoether, RC(=NH)Oalkyl, (where alkyl is C1–C6) derivative of an unsaturated fatty acid, and hydrazoic acid as described in German Pat. No. 521870. The iminoether derivative is obtained by treatment of a nitrile derivative of an unsaturated fatty acid with an alkanol (C1–C6) and a strong acid such as, for example, hydrochloric acid or p-toluenesulphonic acid. The reaction between the iminoether and hydrazoic acid is conducted in the presence of a solvent such as, for example, chloroform or dimethylformamide, at from 0° C. to 120° C., for from 1 to 72 hours. Tetrazole derivatives can also be obtained by the reaction between an amidine derivative of an unsaturated fatty acid, prepared, for example, from the nitrile derivative of an unsaturated fatty acid, as described in *Synthetic Organic Chemistry*, John Wiley and Sons, Publ., New York, 635 (1953) and nitrous acid, as described in *Annalen*, 263, 96 (1981), and 208, 91 (1897). The reaction is conducted in water or a mixture of water and a suitable organic solvent such as, for example, methanol or dioxan, at from 0° C. to 100° C., for from 1 to 24 hours.

Compounds wherein X is C(O)CH2OH are prepared from an appropriate unsaturated fatty acid described above according to the procedure of Reaction Scheme 2.

REACTION SCHEME 2

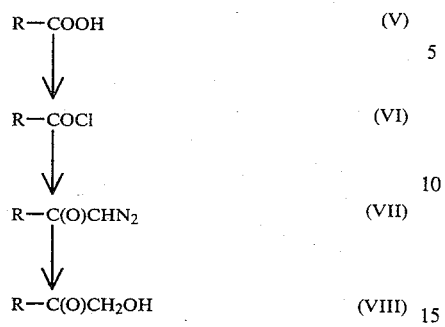

R—COOH is an unsaturated fatty acid of the formula (1), (2) or (3) wherein
A is C=C or C≡C;
B is C=C or C≡C;
D is C—C, C=C, or C≡C;
E is C—C, C=C, or C≡C;
F is C—C, C=C, or C≡C; and
X is COOH.

Preparation of hydroxymethylketone derivatives (VIII) of various unsaturated fatty acids of 18-22 carbon atoms begins with reacting an appropriate unsaturated fatty acid (V), for example arachidonic acid, with a thionyl or phosphoryl halide or a phosphorus pentahalide, preferably thionyl chloride, dissolved in an inert organic solvent, preferably benzene, containing a trace of a tertiary organic amide, preferably dimethylformamide. The mixture is reacted for 8-32 hours, preferably for 16 hours, at from 0° C. to 25° C., then evaporated to dryness. The residue, the acid chloride (VI), is dissolved in an inert organic solvent, preferably ethyl ether. The solution is cooled to −5° C. to 5° C., preferably to 0° C., and an excess of a solution of diazomethane in an ethereal solvent, preferably diethyl ether, is added. The mixture is allowed to react for 1 to 5 hours, preferably 2 hours, then evaporated to dryness, and the residue, the diazoketone (VII), is dissolved in a water miscible ether, preferably tetrahydrofuran. To the solution is added an aqueous solution of a strong acid, preferably trifluoroacetic acid. The mixture is left to react for 2 to 8 hours, preferably 4 hours, and the target compound (VIII) is then isolated and purified by means known in the art.

Hydroxymethylketone derivatives of unsaturated fatty acids can also be prepared by the reaction of an acyl halide, an anhydride or a mixed anhydride derived from an unsaturated fatty acid, and an alkoxy or alkylthio substituted silylated ketene acetal, followed by decarboxylation of the intermediate product, as described in *J. Org. Chem.*, 25, 4617 (1979). The reaction is performed either with or without a suitable organic solvent such as, for example, toluene or diphenyl ether and either with or without the addition of a Lewis acid catalyst such as, for example, stannic chloride, at from 0° C. to 150° C., for from 5 minutes to 8 hours. The decarboxylation reaction is conducted in a suitable solvent such as dioxan, in the presence of an aqueous mineral acid such as hydrochloric acid, at from 0° C. to 100° C., for from 10 minutes to 3 hours. Hydroxymethylketone derivatives of unsaturated fatty acids can also be obtained by hydrolysis, using either acid, such as hydrochloric acid, or base, such as potassium hydroxide, of an acyloxymethylketone (RCOCH$_2$OCO alkyl), or halomethylketone (RCOCH$_2$ halo) derivative of an unsaturated fatty acid, where alkyl is C1-C6 and halo is chloro, bromo or iodo. The reaction is conducted in an aqueous or aqueous organic solvent, such as methanol, ethanol and the like, at from 0 C. to 60 C. for from 1 to 24 hours.

Preparation of unsaturated fatty acid derivatives wherein X is C(O)NHOH is illustrated in Reaction Scheme 3.

REACTION SCHEME 3

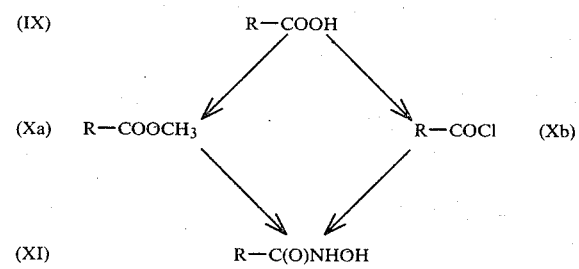

R—COOH is an unsaturated fatty acid of the formula (1), (2) or (3) wherein
A is C=C or C≡C;
B is C=C or C≡C;
D is C—C, C=C, or C≡C;
E is C—C, C=C, or C≡C;
F is C—C, C=C, or C≡C; and
X is COOH.

The acylhydroxylamine derivatives (XI) of the unsaturated fatty acids are prepared in two ways. The acid (IX) is either first converted, as described above, into an acid halide, preferably the acid chloride (Xb), or into a lower alkyl ester (Xa), preferably the methyl ester, by treatment either with a solution of hydrogen chloride in the appropriate lower alkanol, preferably methanol, or with a diazoalkane, preferably diazomethane. The acid chloride or the lower alkyl ester, so obtained, is then reacted with an excess of hydroxylamine in an aqueous organic solvent, preferably aqueous methanol, at a pH of between 7 and 10, preferably at pH 9, for from ¼ to 6 hours, preferably about 1 hour. The acylhydroxylamine product (XI) is then isolated by means known in the art.

Acylhydroxylamines can also be prepared by the reaction between hydroxylamine and an activated derivative of an unsaturated fatty acid such as, for example, an acyl halide, an anhydride, a mixed anhydride, an alkyl ester, a substituted or unsubstituted phenyl ester, a thioalkyl ester, a thiophenyl ester, an acyl imidazole, and the like. The reaction is conducted in an aqueous organic or organic solvent such as, for example, methanol, acetonitrile or acetone, at from 0° C. to the reflux temperature of the solvent, for from 1 to 48 hours. Alternately, acylhydroxylamines can be prepared by acid-catalyzed rearrangement of a primary nitro derivative of an unsaturated fatty acid (RNO$_2$) as described in *Chemical Reviews*, 32, 395 (1943). The reaction is conducted in an aqueous organic or organic solvent, such as, for example, methanol, ethanol and dioxan, at from 0° C. to 100° C., for from 1 to 24 hours, in the presence of a strong acid such as, for example, sulphuric acid or hydrochloric acid. Acylhydroxylamine derivatives of unsaturated fatty acids can also be obtained by the oxidation of the oxime derivative (RCH=NOH) of an unsaturated fatty aldehyde (RCHO), using, for example, hydrogen peroxide as described in *Chemical Reviews*, 33, 225 (1943). The reaction is conducted in a solvent such as methanol or dichloromethane and the like, at from 0° C. to 35° C. for from 1 to 6 hours.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures could, of course, also be used.

Salts of the compounds of formula (1), (2), or (3) may be interchanged by taking advantage of differential solubilities of the salts, or by treating with the appropriately loaded ion exchange resin.

The salts of acylhydroxylamine or tetrazole derivatives of the compounds of formula (1), (2) or (3) are prepared by treating the acylhydroxylamine or tetrazole compound of formula (1), (2), or (3) with at least one molar equivalent of a pharmaceutically acceptable base. Representative pharmaceutically acceptable bases are sodium hydroxide, potassium hydroxide, ammonium hydroxide, calcium hydroxide, metal alkoxides, for example, sodium methoxide, trimethylamine, lysine, caffeine, and the like. The reaction is conducted in water, alone or in combination with an inert, water-miscible organic solvent, or in a suitable organic solvent such as methanol, ethanol, and the like, at a temperature of from about 0° C. to about 100° C., preferably at room temperature. Typical inert, water-miscible organic solvents include methanol, ethanol, or dioxane. The molar ratios of compounds of Formula (1), (2), or (3) to base used are chosen to provide the ratio desired for any particular salt.

Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, tromethamine, dicyclohexylamine, choline and caffeine.

The salt products are also isolated by conventional means. For example, the reaction mixtures may be evaporated to dryness, and the salts can be further purified by conventional methods.

UTILITY AND ADMINISTRATION

The compounds of the present invention are tetrazole, acylhydroxylamine, hydroxymethylketone and amide derivatives of unsaturated fatty acids. These compounds display a spectrum of biological activities affecting the enzymatic processes leading to the in vivo synthesis of certain compounds or agents such as prostaglandins or leukotrienes, or platelet aggregation inducing compounds. The compounds of this invention show selective inhibitory activity on the enzymes involved in the metabolic pathways of prostaglandins or leukotrienes, namely they are selective inhibitors of lipoxygenases and cyclooxygenases.

Because of their biological activities, these compounds are promising agents for prophylactic and/or therapeutic use particularly in the treatment of inflammatory disorders such as, for example, rheumatoid arthritis and osteoarthritis, or in the prevention or treatment of disorders of allergic origin such as, for example, bronchospastic symptoms in asthma. The compounds are also useful for the alleviation of pain.

Administration of the active compounds in the pharmaceutical composition described hereinafter can be via any of the accepted modes of administration for agents which affect inflammation, pain or allergy. These methods include oral, parenteral and otherwise systemic administration, or topical administration. Depending on the intended mode, the composition may be in the form of solid, semi-solid or liquid dosage forms, such as, for example, tablets, suppositories, pills, capsules, powders, liquids, suspension, or the like, preferably in unit dosage forms suitable for single administration of precise dosages. The composition will include a conventional pharmaceutical carrier or excipient and an active compound of formula (1), (2), or (3) and/or the pharmaceutically acceptable salts thereof and, in addition, may include other medicinal agents, pharmaceutical agents, carriers, adjuvants, etc.

The amount of active compound administered will of course, be dependent on the subject being treated, the severity of the affliction, the manner of administration and the judgment of the prescribing physician. However, an effective dosage will be in the range of 0.001–50 mg/kg/day, preferably 0.01–10 mg/kg/day. For an average 70 kg human, this would amount to 0.07–3300 mg per day, or preferably 0.7–700 mg/day.

The novel compounds of this invention may be formulated with suitable pharmaceutical vehicles known in the art to form particularly effective anti-inflammatory, anti-allergic and analgesic compositions. Generally, an effective amount of active ingredient is about 0.001% w/w to about 10% w/w of the total formulated composition. The rest of the formulated composition will be about 90% w/w to about 99.999% w of a suitable excipient.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s) in an amount effective to alleviate the symptoms of the subject being treated.

For oral administration, a pharmaceutically acceptable, non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%–95% active ingredient, preferably 25–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

For systemic administration via suppository, traditional binders and carriers include, e.g. polyalkylene glycols or triglycerides. Such suppositories may be formed from mixtures containing active ingredient in the range of 0.5%–10%; preferably 1–2%.

For aerosol administration, the active ingredient is preferably supplied in finely divided form along with a surfactant and a propellant. Typical percentages of active ingredients are 0.01 to 20% by weight, preferably 0.04 to 1.0%.

Surfactants must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olestearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the trademark "Spans") and the polyoxyethylene and polyoxypropylene derivatives of these esters. Mixed esters, such as mixed or natural glycerides may be employed. The preferred surface-active agents are the oleates or sorbitan, e.g., those sold under the trademarks "Arlacel C" (Sorbitan sesquioleate), "Span 80" (sorbitan monooleate) and "Span 85" (sorbitan trioleate). The surfactant may constitute 0.1–20% by weight of the composition, preferably 0.25–5%.

The balance of the composition is ordinarily propellant. Liquefied propellants are typically gases at ambient conditions, and are condensed under pressure. Among suitable liquefied propellants are the lower alkanes containing up to five carbons, such as butane and propane; and preferably fluorinated or fluorochlorinated alkanes, such as are sold under the trademark "Freon." Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

The following Preparations and Examples serve to illustrate the invention and make the invention enabling. They should not be construed as narrowing it or limiting its scope in any way.

EXAMPLE 1

A. Preparation of 1-(Tetrahydropyranyloxy)-hex-2(Z)-en-5-yne

To a solution of hex-2(Z)-en-5-yn-1-ol (5 g) in methylene chloride (100 ml) at O is added phosphorus oxychloride (0.1 ml) and 5 g of dihydropyran. After 2 hours, the solution is added to saturated aqueous sodium carbonate. The organic solution is dried and evaporated to yield the title compound as an oil.

B. Preparation of 1-(Tetrahydropyranyloxy)-tetradec-2(Z),8(Z)-dien-5-yne

1-Tetrahydropyranyloxy)-hex-2(Z)-en-5-yne (1.8 g) is dissolved in 1:2 aqueous ethanol (25 ml) and to the solution is added cuprous chloride (0.2 g) and sufficient 50% aqueous sodium hydroxide to produce a pH of 9. The mixture is heated to 60 and 1-bromooct-2(Z)-ene (1.9 g) is added over a period of 2 hours, with simultaneous addition of sufficient 50% aqueous sodium hydroxide to maintain a pH of 8–9. After a further 3 hours, the mixture is cooled, diluted with water, and extracted with ether. The extract is washed, dried and evaporated, and the crude product is chromatographed on silica gel, eluting with benzene/triethylamine (300/1), so as to produce the title compound as an oil.

EXAMPLE 2

Preparation of 1-Hydroxytetradeca-2(Z),8(Z)dien-5-yne p-Toluenesulphonic acid monohydrate (30 mg) was added to a solution of 1-(tetrahydroxypyranyloxy)tetradeca-2(Z),8(Z)-dien-5-yne (1.1 g) in methanol (30 ml). The mixture was kept at 25 C. for 2 hours, then ether and water were added. The organic solution was washed, dried and evaporated to yield the title compound as an oil.

EXAMPLE 3

Preparation of 1-Bromotetradeca-2(Z),8(Z)-dien-5-yne

1-Hydroxytetradeca-2(Z),8(Z)-dien-5-yne (600 mg) was dissolved in methylene chloride (10 ml) and to the solution was added triphenylphosphine (600 mg) and cyanogen bromide (200 mg). After 2½ hours the methylene chloride was removed under vacuum and the residue was extracted with 10 ml of hexane/ether (10/1;v/v). The solution was filtered through silica gel (2 g) and evaporated to yield the title compound as an oil.

EXAMPLE 4

Preparation of Eicosa-8(Z),14(Z)-diene5,11-diynoic acid

To a solution of hex-5-ynoic acid (448 mg) in tetrahydrofuran (10 ml) was added ethereal ethylmagnesium bromide (2.7 ml of a 3.0 molar solution). The mixture was refluxed for 1 hour, then cuprous chloride (10 mg) and 1-bromotetradeca-2(Z),8(Z)-dien-5-yne (550 mg) were added. The reaction was refluxed for 24 hours, then cooled and dilute hydrochloric acid and ether were added. The organic layer was dried and evaporated, and the residue was chromatographed on silica gel, eluting with hexane/ether/acetic acid, (200/200/1;v/v/v) so as to afford the title compound as an oil.

EXAMPLE 5

Preparation of 5-(Nonadeca-4(Z),7(Z),10(Z),13(z)-tetraenyl)-1-H-tetrazole

A. Preparation of Eicosa-5(Z),8(Z),11(Z),14(Z)-tetraenamide

Carbonyldiimidazole (1.97 g) was added to a solution of eicosa-5(Z),8(Z),11(Z),14(Z)-tetraenoic acid (3.3 g) in dichloromethane (70 ml). After 4 hours concentrated ammonium hydroxide (10 ml) was added and the mixture was stirred vigorously for 48 hours. The organic solution was separated, dried and evaporated to yield the title compound as a solid, m.p.: ca. 35° C.

B. Preparation of Eicosa-5(Z),8(Z),11(Z),14(Z) tetraenenitrile p-Toluenesulphonyl chloride (1.54 g) was added to a solution of eicosa-5(Z),8(Z),11(Z),14(Z)-tetraenamide (2.4 g) in pyridine (50 ml). After 24 hours, the solution was poured into water. The aqueous solution was extracted with ether, and the extract was washed with dilute hydrochloric acid, dried and evaporated to give the title compound as an oil.

C. Preparation of 5-(Nonadeca-4(Z),7(Z),10(Z),13(Z)tetraenyl-1-H-tetrazole

Eicosa-5(Z),8(Z),11(Z),14(Z)-tetraenenitrile (1.4 g), sodium azide (1.06 g) and ammonium chloride (0.85 g) were heated at 100° C. in dimethylformamide (8 ml) for 23 hours. The solution was cooled and diluted with ether (50 ml). The ethereal solution was washed with water then extracted with dilute aqueous potassium hydroxide. The aqueous extract was acidified with dilute hydrochloric acid, and extracted with ether. The extract was dried and evaporated to afford the title compound as an oil.

EXAMPLE 6

Preparation of Tetrazole Derivatives of Various Unsaturated Fatty Acids

Similarly, by using the procedure of Example 5, Sections A, B and C, but substituting eicosa-5(Z),8(Z),-11(Z),14(Z)-tetraenoic acid with the following starting materials:
eicosa-5,8,11,14-tetraynoic acid;
heneicosa-5(Z),8(Z),11(Z),14(Z)-tetraenoic acid;
heneicosa-5,8,11,14-tetraynoic acid;
nonadeca-5(Z),8(Z),11(Z),14(Z)-tetraenoic acid;
nonadeca-5,8,11,14-tetraynoic acid;
docosa-5(Z),8(Z),11(Z),14(Z)-tetranoic acid;
docosa-5,8,11,14-tetraynoic acid;
eicosa-6,9,12,15-tetraynoic acid;
docosa-6,9,12,15-tetraynoic acid;
eicosa-4,7,10,13-tetraynoic acid;
docosa-4,7,10,11-tetraynoic acid;
docosa-7,10,14,17-tetraynoic acid;
heneicosa-8,11,14,16-tetraynoic acid;
eicosa-5,8,11-triynoic acid;
nonadeca-8,11,14-triynoic acid;
heneicosa-8(Z),14(Z)-diene-5,11-diynoic acid;
heneicosa-8(Z),11(Z),14(Z)-triene-5-ynoic acid; and
heneicosa-5(Z),8(Z),14(Z)-triene-11-ynoic acid;
there are obtained respectively:
5-(nonadeca-4,7,10,13-tetraynyl)-1-H-tetrazole;
5-(eicosa-4(Z),7(Z),10(Z),13(Z)-tetraenyl)-1-H-tetrazole;
5-(eicosa-4,7,10,13-tetraynyl)-1-H-tetrazole;
5-(octadeca-4(Z),7(Z),10(Z),13(Z)-tetraenyl)-1H-tetrazole;
5-(octadeca-4,7,10,13-tetraynyl)-1-H-tetrazole;
5-(heneicosa-4(Z),7(Z),10(Z),13(Z)-tetraenyl)-1-H-tetrazole;
5-(heneicosa-4,7,10,13-tetraynyl)-1-H-tetrazole;
5-(nonadeca-5,8,11,14-tetraynyl)-1-H-tetrazole;
5-(heneicosa-5,8,11,14-tetraynyl)-1-H-tetrazole;
5-(nonadeca-3,6,9,12-tetraynyl)-1-H-tetrazole;
5-(heneicosa-3,6,9,12-tetraynyl)-1-H-tetrazole;
5-(heneicosa-6,9,13,16-tetraynyl)-1-H-tetrazole;
5-(eicosa-7,10,13,16-tetraynyl)-1-H-tetrazole;
5-(nonadeca-4,7,10-triynyl)-1-tetrazole;
5-(octadeca-7,10,13-triynyl)1-H-tetrazole;
5-(eicosa-7(Z),13(Z)-diene-4,10-diynyl)-1-H-tetrazole;
5-(eicosa-7(Z),10(Z),13(Z)-trien-4-ynyl)-1-H-tetrazole; and
5-(eicosa-4(Z),7(Z),13(Z)-trien-10-ynyl)-1-H-tetrazole.

EXAMPLE 7

Preparation of Eicosa-5(Z),8(Z),11(Z),14(Z)-tetraenoylhydroxylamine

Hydroxylamine hydrochloride (0.95 g) was dissolved in water (2.1 ml) and methanol (1.65 ml) and 10N aqueous sodium hydroxide (2.7 ml ) were added. The resultant solution was added to a solution of methyl eicosa-5(Z),8(Z),11(Z),14(Z)-tetraenoate (1.22 g) in methanol (21 ml). After 1 hour the mixture was acidified to pH 5 with hydrochloric acid, and then extracted with ether. The extract was dried and evaporated and the residue was chromatographed on silica gel, eluting with methylene chloride/methanol/ammonium hydroxide (40/5/0.3;v/v/v), to afford the title compound as an oil.

EXAMPLE 8

Preparation of Acylhydroxylamine Derivatives of Various Unsaturated Fatty Acids

Similarly, by using the procedure of Example 7 but substituting methyl eicosa-5(Z),8(Z),11(Z),14(Z)-tetraenoate with the following starting materials;
methyl heneicosa-5(Z),8(Z),11(Z),14(Z)-tetraenoate;
methyl nonadeca-5(Z),8(Z),11(Z),14(Z)-tetraenoate;
methyl docosa-5(Z),8(Z),11(Z),14(Z)-tetraenoate;
methyl heneicosa-8(Z),14(Z)-diene-5,11-diynoate;
methyl heneicosa-8(Z),11(Z),14(Z)-trien-5-ynoate; and
methyl heneicosa-5(Z),8(Z),14(Z)-trien-11-ynoate;

there are obtained, respectively:
heneicosa-5(Z),8(Z),11(Z),14(Z)-tetraenoyl hydroxylamine;
nonadeca-5(Z),8(Z),11(Z),14(Z)-tetraenoyl hydroxylamine;
docosa-5(Z),8(Z),11(Z),14(Z)-tetraenoyl hydroxylamine;
heneicosa-8(Z),14(Z)-diene-5,11-diynoylhydroxylamine;
heneicosa-8(Z),11(Z),14(Z)-trien-5-ynoyl-hydroxylamine; and
heneicosa-5(Z),8(Z),14(Z)-trien-11-ynoyl-hydroxylamine.

EXAMPLE 9

Preparation of Heneicosa-5,8,11,14-tetraynoylhydroxylamine

Heneicosa-5,8,11,14-tetraynoic acid (130 mg) was dissolved in methylene chloride (3 ml) and a solution of thionyl chloride (104 mg) and dimethylformamide (5 mg) in methylene chloride (2.6 ml) was added. After 3 hours at 25° C., the solution was evaporated. To the residue was added a solution of hydroxylamine hydrochloride (58 mg) and sodium bicarbonate (70 mg) in water (0.4 ml) and methanol (0.4 ml) to which had been added normal aqueous potassium hydroxide sufficient to obtain a pH of 9. After 10 minutes ether (20 ml) and 1.0N hydrochloric acid (10 ml) were added. The organic solution was dried and evaporated, and the residue was chromatographed on silica gel, eluting with methylene chloride/methanol/ammonium hydroxide, (40/4/0.3;v/v/v) so as to afford the title compound as a solid, m.p.: 85°–88° C.

EXAMPLE 10

Preparation of Hydroxylamine Derivatives of Various Unsaturated Fatty Acids

Similarly, by using the procedure of Example 9, but substituting heneicosa-5,8,11,14-tetraynoic acid with the following starting materials;
eicosa-5,8,11,14-tetraynoic acid;
nonadeca-5,8,11,14-tetraynoic acid;
docosa-5,8,11,14-tetraynoic acid;
eicosa-6,9,12,15-tetraynoic acid;
docosa-6,9,12,15-tetraynoic acid;
eicosa-4,7,10,13-tetraynoic acid;
docosa-4,7,10,13-tetraynoic acid;
docosa-7,10,13,16-tetraynoic acid;
heneicosa-7,10,13,16-tetraynoic acid;
nonadeca-8,11,14-triynoic acid; and
eicosa-5,8,11-triynoic acid;
there are obtained, respectively:
eicosa-5,8,11,14-tetraynoylhydroxylamine;
nonadeca-5,8,11,14-tetraynoylhydroxylamine;
docosa-5,8,11,14-tetraynoylhydroxylamine;
eicosa-6,9,12,15-tetraynoylhydroxylamine;
docosa-6,9,12,15-tetraynoylhydroxylamine;
eicosa-4,7,10,13-tetraynoylhydroxylamine;
docosa-4,7,10,13-tetraynoylhydroxylamine;
docosa-7,10,13,16-tetraynoylhydroxylamine;
heneicosa-7,10,13,16-tetraynoylhydroxylamine;
nonadeca-8,11,14-triynoylhydroxylamine; and
eicosa-5,8,11-triynoylhydroxylamine.

EXAMPLE 11

Preparation of 1-Hydroxyheneicosa-6(Z),9(Z),12(Z),15(Z)tetraen-2-one

Eicosa-5(Z),8(Z),11(Z),14(Z)-tetraenoic acid (0.5 g) was added to benzene (50 ml) containing thionyl chloride (0.125 ml) and dimethylformamide (0.05 ml). After 16 hours the solution was evaporated to dryness under vacuum, and the residue was dissolved in ether. The solution was cooled to 0° C. and excess ethereal diazomethane was added. After 2 hours the solution was evaporated to dryness under vacuum and the residue was dissolved in tetrahydrofuran (10 ml). To the resulting solution was added a mixture of water (5 ml) and trifluoroacetic acid (1 ml). The reaction was left for 4 hours, and then diluted with water and extracted with hexane. The extract was dried and evaporated, and the residue was chromatographed on silica gel, eluting with hexane/ether (3/1;v/v), to afford the title compound as an oil.

EXAMPLE 12

Preparation of Hydroxymethylketone Derivatives of Various Unsaturated Fatty Acids Similarly, by using the procedure of Example 11, but substituting eicosa 5(Z),8(Z),11(Z),14(Z)-tetraenoic acid with the following starting materials:
eicosa-5,8,11,14-tetraynoic acid;
nonadeca 5(Z),8(Z),11(Z),14(Z)-tetraenoic acid;
nonadeca 5,8,11,14-tetraynoic acid;
octadeca-5(Z),8(Z),11(Z),14(Z)-tetraenoic acid;
octadeca-4,7,10,13-tetraynoic acid;
heneicosa-4(Z),7(Z),10(Z),13(Z)-tetraenoic acid;
heneicosa-4,7,10,13-tetraynoic acid;
nonadeca-5,8,11,14-tetraynoic acid;
heneicosa-5,8,11,14-tetraynoic acid;
nonadeca-3,6,9,12-tetraynoic acid;
heneicosa-3,6,9,12-tetraynoic acid;
heneicosa-6,9,12,15-tetraynoic acid;
eicosa-7,10,13,16-tetraynoic acid;
nonadeca-4,7,10-triynoic acid; and
octadeca-7,10,13-triynoic acid.
heneicosa-8(Z),14(Z)-diene-5,11-diynoic acid;
heneicosa-8(Z),11(Z),14(Z)-trien-5-ynoic acid; and
heneicosa-5(Z),8(Z),14(Z)-trien-11ynoic acid;
there are obtained, respectively:
1-hydroxyheneicosa-6,9,12,15-tetrayn-2-one;
1-hydroxyeicosa-6(Z),9(Z),12(Z),15(Z)-tetraen-2-one;
1-hydroxyeicosa-6,9,12,15-tetrayn-2-one;
1-hydroxynonadeca-6(Z),9(Z),12(Z),15(Z)-tetraen-2-one;
1-hydroxynonadeca-5,8,11,14-tetrayn-2-one;
1-hydroxydocosa-5(Z),8(Z),11(Z),14(Z)-tetraen-2-one;
1-hydroxydocosa-5,8,11,14-tetrayn-2-one;
1-hydroxyeicosa-6,9,12,15-tetrayn-2-one;
1-hydroxydocosa-6,9,12,15-tetrayn-2-one;
1-hydroxyeicosa-4,7,10,13-tetrayn-2-one;
1-hydroxydocosa-4,7,10,13-tetrayn-2-one;
1-hydroxydocosa-7,10,13,16-tetrayn-2-one;
1-hydroxyheneicosa-8,11,14,17-tetrayn-2-one;
1-hydroxyeicosa-5,8,11-triyne-2-one;
1-hydroxynonadeca-8,11,14-triyne-2-one;
1-hydroxydocosa-9(Z),15(Z)-diene-6,12-diyn-2-one;
1-hydroxydocosa-9,12,15-triene-6-yn-2-one; and
1-hydroxydocosa-6(Z),9(Z),15(Z)-triene-12-yn-2-one.

EXAMPLE 13

Conversion of 5-(Eicosa-4,7,10,13-tetraynyl)-1H-tetrazole into the Sodium Salt

Sodium methoxide (82 mg) is added to a solution of 5-(eicosa-4,7,10,13-tetraynyl)-1-H-tetrazole (500 mg) in methanol (5 ml). The solution is then evaporated to dryness to afford 5-(eicosa-4,7,10,13-tetraynyl)-1-H-tetrazole sodium salt.

In a similar manner, all compounds of formula (1), (2) or (3), wherein X is 1-H-tetrazol-5-yl or C(O)NHOH, in free acid form, may be converted to salts such as potassium, lithium, ammonium, calcium, magnesium, ferrous, zinc, copper, manganous, aluminum, ferric, manganic salts and the like.

EXAMPLE 14

Conversion of 5-(Eicosa-4,7,10,13-tetraynyl) 1-H-tetrazole Sodium Salt into 5-(Eicosa-4,7,10,13-tetraynyl)-1-H-tetrazole A two-fold stoichiometric excess of N-hydrochloric acid is added to a solution of 5-(eicosa-4,7,10,13-tetraynyl)-1-H-tetrazole in water. The solution is then extracted with ether, and the extract is dried and evaporated to afford 5-(eicosa-4,7,10,13-tetraynyl)-1-H-tetrazole.

In Examples 15 through 22 the active ingredient is heneicosa-5,8,11,14-tetraynoylhydroxylamine. Other compounds of formula (1), (2), or (3) and the pharmaceutically acceptable salts thereof may be substituted therein.

EXAMPLE 15

| Ingredients | Quantity per tablet, mgs. |
| --- | --- |
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 16

| Ingredients | Quantity per tablet, mgs. |
| --- | --- |
| Active ingredient | 100 |
| lactose, spray-dried | 148 |
| magnesium stearate | 2 |

The above ingredients are mixed and introduced into a hard-shell gelatin capsule.

EXAMPLE 17

| Ingredients | Quantity per tablet, mgs. |
| --- | --- |
| Active ingredient | 200 |
| cornstarch | 50 |
| lactose | 145 |
| magnesium stearate | 5 |

The above ingredients are mixed intimately and pressed into single scored tablets.

EXAMPLE 18

| Ingredients | Quantity per tablet, mgs. |
| --- | --- |
| Active ingredient | 108 |
| lactose | 15 |
| cornstarch | 25 |
| magnesium stearate | 2 |

The above ingredients are mixed and introduced into a hard-shell gelatin capsule.

EXAMPLE 19

| Ingredients | Quantity per tablet, mgs. |
| --- | --- |
| Active ingredient | 150 |
| lactose | 92 |

The above ingredients are mixed and introduced into a hard-shell gelatin capsule.

EXAMPLE 20

An injectable preparation buffered to a pH of 7 is prepared having the following composition:

| Ingredients | |
| --- | --- |
| Active ingredient | 0.2 g |
| $KH_2PO_4$ buffer (0.4 M solution) | 2 ml |
| KOH (1 N) | q.s. to pH 7 |
| water (distilled, sterile) | q.s. to 20 ml |

EXAMPLE 21

An oral suspension is prepared having the following composition:

| Ingredients | |
| --- | --- |
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

EXAMPLE 22

Topical Formulation is prepared having the following composition:

| Ingredients | grams |
| --- | --- |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water q.s. | 100 |

All of the above ingredients, except water, are combined and heated to 60° C. with stirring. A sufficient quantity of water at 60° C. is then added with vigorous stirring to emulsify the ingredients, and water then added q.s. 100 g.

What is claimed is:

1. A compound chosen from those represented by the formulas

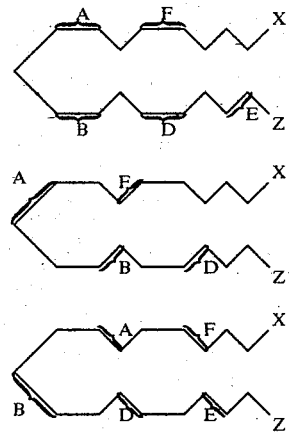

and their pharmaceutically acceptable, non-toxic salts wherein

A is C=C or C≡C;
B is C=C or C≡C;
D is C—C, C=C, or C≡C;
E is C—C, C=C, or C≡C;
F is C—C, C=C, or C≡C;
Z is CH$_3$, CH$_2$CH$_3$, —CH$_2$CH$_2$CH$_3$; CH$_2$CH$_2$CH$_2$CH$_3$; and
X is C(O)NHOH.

2. The compound of claim 1 and the pharmaceutically acceptable, non-toxic salts thereof, wherein the compound is represented by formula (1).

3. The compound of claim 2 and the pharmaceutically acceptable, non-toxic salts thereof, wherein Z is —CH$_2$CH$_3$.

4. The compound of claim 3 and the pharmaceutically acceptable, non-toxic salts thereof, wherein X is C(O)NHOH, namely eicosa-5(Z),8(Z), 11(Z),14(Z)-tetraenoylhydroxylamine.

5. The compound of claim 3 and the pharmaceutically acceptable, non-toxic salts thereof, wherein X is C(O)NHOH, namely eicosa-5,8,11,14-tetraynoylhydroxylamine.

6. The compound of claim 2 and the pharmaceutically acceptable, non-toxic salts thereof, wherein Z is —CH$_2$CH$_2$CH$_3$.

7. The compound of claim 6 and the pharmaceutically acceptable, non-toxic salts thereof, wherein X is C(O)NHOH, namely heneicosa-5(Z),8(Z),11(Z),14(Z)-tetraenoylhydroxylamine.

8. The compound of claim 6 and the pharmaceutically acceptable, non-toxic salts thereof, wherein X is C(O)NHOH, namely heneicosa-5,8,11,14-tetraynoylhydroxylamine.

9. The compound of claim 2 and the pharmaceutically acceptable, non-toxic salts thereof, wherein Z is —CH$_3$.

10. The compound of claim 9 and the pharmaceutically acceptable, non-toxic salts thereof, wherein A, B, D, and F are C=C and E is C—C.

11. The compound of claim 9 and the pharmaceutically acceptable, non-toxic salts thereof, wherein X is C(O)NHOH, namely nonadeca-5,8,11,14-tetraynoylhydroxylamine.

12. The compound of claim 2 and the pharmaceutically acceptable, non-toxic salts wherein Z is —CH$_2$CH$_2$CH$_2$CH$_3$.

13. The compound of claim 12 and the pharmaceutically acceptable, non-toxic salts thereof, wherein A, B, D, and F are C=C and E is C—C.

14. The compound of claim 12 and the pharmaceutically acceptable, non-toxic salts, wherein X is C(O)NHOH, namely docosa-5,8,11,14-tetraynoylhydroxylamine.

15. The compound of claim 1 and the pharmaceutically acceptable, non-toxic salts thereof, wherein the compound is represented by formula (2).

16. The compound of claim 15 and the pharmaceutically acceptable, non-toxic salts thereof, wherein A, B, D, and F are C≡C.

17. The compound of claim 16 and the pharmaceutically acceptable, non-toxic salts thereof, wherein Z is —CH$_2$CH$_3$.

18. The compound of claim 16 and the pharmaceutically acceptable, non-toxic salts thereof, wherein Z is —CH$_2$CH$_2$CH$_2$CH$_3$.

19. The compound of claim 1 and the pharmaceutically acceptable, non-toxic salts thereof, wherein the compound is represented by formula (3).

20. The compound of claim 19 and the pharmaceutically acceptable, non-toxic salts thereof, wherein Z is —CH$_2$CH$_3$.

21. The compound of claim 19 and the pharmaceutically acceptable, non-toxic salts thereof, wherein Z is —CH$_2$CH$_2$CH$_2$CH$_3$.

22. The compound of claim 21 and the pharmaceutically acceptable, non-toxic salts thereof, wherein X is C(O)NHOH, namely docosa-4,7,10,13-tetraynoylhydroxylamine.

23. The compound of claim 19 and the pharmaceutically acceptable, non-toxic salts thereof, wherein A, B, D, and E are C≡C; F is C—C, and Z is —CH$_2$CH$_2$CH$_2$CH$_3$.

24. The compound of claim 6 and the pharmaceutically acceptable, non-toxic salts thereof, wherein A, B, D and E are C≡C and F is C—C.

25. The compound of claim 3 and the pharmaceutically acceptable, non-toxic salts thereof, wherein A, B and F are C≡C and D and E are C—C.

26. The compound of claim 25 and the pharmaceutically acceptable, non-toxic salts thereof, wherein X is C(O)NHOH, namely eicosa-5,8,11-triynoylhydroxylamine.

27. The compound of claim 2, wherein A and D are C=C; B and F are C≡C; E is C—C; and Z is CH$_2$CH$_3$; CH$_2$CH$_2$CH$_3$ or CH$_2$CH$_2$CH$_2$CH$_3$.

28. The compound of claim 27 wherein X is C(O)NHOH and Z is CH$_2$CH$_2$CH$_3$, namely heneicosa-8(Z),14(Z)-diene-5,11-diynoylhydroxylamine.

29. The compound of claim 2, wherein A, B and D are C=C, E is C—C, F is C≡C and Z is CH$_2$CH$_3$, CH$_2$CH$_2$CH$_3$ or CH$_2$CH$_2$CH$_2$CH$_3$.

30. The compound of claim 29, wherein X is C(O)NHOH and Z is CH$_2$CH$_2$CH$_3$, namely heneicosa-8(Z),11(Z),14(Z)-triene-5-ynoylhydroxylamine.

31. The compound of claim 2, wherein A, D and F are C=C, B is C≡C, E is C—C and Z is CH$_2$CH$_3$, CH$_2$CH$_2$CH$_3$, CH$_2$CH$_2$CH$_2$CH$_3$.

32. The compound of claim 31, wherein X is C(O)N-HOH and Z is CH₂CH₂CH₃, namely heneicosa-5(Z),8(Z),14(Z)-trien-11-ynoylhydroxylamine.

33. A pharmaceutical composition for preventing or treating inflammation and/or pain and allergic reactions in mammals which composition comprises a compound of claim 1 or a pharmaceutically acceptable, non-toxic salt thereof in admixture with at least one pharmaceutically acceptable excipient.

34. A method for preventing or treating inflammation and/or pain and allergic reactions in mammals which method comprises administering to a subject in need of such treatment a therapeutically effective amount of a compound of claim 1 or a pharmaceutically acceptable, non-toxic salt thereof.

35. A compound chosen from those represented by the formulas

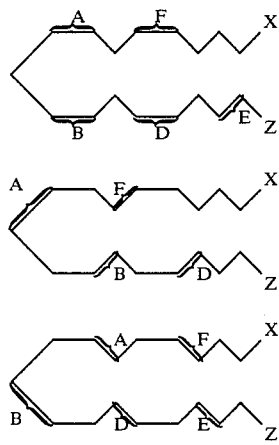

and their pharmaceutically acceptable, non-toxic salts wherein

A is C=C or C≡C;
B is C=C or C≡C;
D is C—C, C=C, or C≡C;
E is C—C, C=C, or C≡C;
F is C—C, C=C, or C≡C;
Z is CH₃, CH₂CH₃, —CH₂CH₂CH₃; CH₂CH₂CH₂CH₃; X is CONH₂ and at least one of A, B, D, or F is C≡C.

36. The compound of claim 35 and the pharmaceutically acceptable, non-toxic salts thereof, wherein the compound is represented by formula (1).

37. The compounds of claim 36 and the pharmaceutically acceptable, non-toxic salts thereof, wherein Z is —CH₂CH₃.

38. The compound of claim 36 and the pharmaceutically acceptable non-toxic salts thereof, wherein A, B, D, and F are C≡C, and E is C—C.

39. The compound of claim 36 and the pharmaceutically acceptable, non-toxic salts thereof, wherein Z is —CH₂CH₂CH₃.

40. The compound of claim 39 and the pharmaceutically acceptable, non-toxic salts thereof, wherein A, B, D, and F are C≡C, and E is C—C.

41. The compound of claim 36 and the pharmaceutically acceptable, non-toxic salts thereof, wherein Z is —CH₃.

42. The compound of claim 36 and the pharmaceutically acceptable, non-toxic salts wherein Z is —CH₂CH₂CH₂CH₃.

43. The compound of claim 35 and the pharmaceutically acceptable, non-toxic salts thereof, wherein the compound is represented by the formula (2).

44. The compound of claim 43 and the pharmaceutically acceptable, non-toxic salts thereof, wherein A, B, D, and F are C≡C.

45. The compound of claim 43 and the pharmaceutically acceptable, non-toxic salts thereof, wherein Z is —CH₂CH₃.

46. The compound of claim 43 and the pharmaceutically acceptable, non-toxic salts thereof, wherein Z is —CH₂CH₂CH₂CH₃.

47. The compound of claim 35 and the pharmaceutically acceptable, non-toxic salts thereof, wherein the compound is represented by the formula (3).

48. The compound of claim 47 and the pharmaceutically acceptable, non-toxic salts thereof, wherein A, B, D, and F are C≡C and E is C—C.

49. The compound of claim 47 and the pharmaceutically acceptable, non-toxic salts thereof, wherein Z is —CH₂CH₃.

50. The compound of claim 48 and the pharmaceutically acceptable, non-toxic salts thereof, wherein Z is —CH₂CH₂CH₂CH₃.

51. The compound of claim 47 and the pharmaceutically acceptable, non-toxic salts thereof, wherein A, B, D, and E are C≡C, and Z is —CH₂CH₂CH₂CH₃.

52. The compound of claim 39 and the pharmaceutically acceptable, non-toxic salts thereof, wherein A, B, D and E are C≡C and F is C—C.

53. The compound of claim 37 and the pharmaceutically acceptable, non-toxic salts thereof, wherein A, B and F are C≡C and D and E are C—C.

54. The compound of claim 41 and the pharmaceutically acceptable, non-toxic salts thereof, wherein A, B, and D are C≡C and E and F are C—C.

55. The compound of claim 36 wherein A and D are C=C; B and F are C≡C; E is C—C; and Z is CH₂CH₃; CH₂CH₂CH₃ or CH₂CH₂CH₂CH₃.

56. The compound of claim 36 wherein A, B and D are C=C, E is C—C, F is C≡C and Z is CH₂CH₃, CH₂CH₂CH₃ or CH₂CH₂CH₂CH₃.

57. The compound of claim 36 wherein A, D and F are C=C, B is C≡C, E is C—C and Z is CH₂CH₃, CH₂CH₂CH₃ or CH₂CH₂CH₂CH₃.

58. A method for preventing or treating inflammation and/or pain or allergic reactions in mammals which method comprises administering to a subject in need of such treatment a therapeutically effective amount of a compound of claim 35 or a pharmaceutically acceptable, non-toxic salt thereof.

59. The compound of claim 35, wherein X is CONH₂ and Z is CH₂CH₃, namely eicosa-5,8,11,14-tetraynamide.

60. The compound of claim 35 wherein X is CONH₂ and Z is CH₂—CH₂—CH₃, namely heneicosa-5,8,11,14-tetraynamide.

* * * * *